United States Patent
Matsushita et al.

(10) Patent No.: US 10,349,831 B2
(45) Date of Patent: Jul. 16, 2019

(54) EYEBALL OPTICAL MEASURING INSTRUMENT, EYEBALL OPTICAL MEASURING METHOD, AND METHOD FOR IRRADIATING AN EYEBALL AND DETECTING LIGHT COMING FROM EYEBALL

(71) Applicant: FUJI XEROX CO., LTD., Tokyo (JP)

(72) Inventors: Kazuyuki Matsushita, Ebina (JP); Kazutaka Takeda, Ebina (JP); Kohei Yukawa, Ebina (JP); Hideaki Ozawa, Ebina (JP); Taku Kinoshita, Ebina (JP); Hideo Nakayama, Ebina (JP)

(73) Assignee: FUJI XEROX CO., LTD., Tokyo (JP)

( * ) Notice: Subject to any disclaimer, the term of this patent is extended or adjusted under 35 U.S.C. 154(b) by 143 days.

(21) Appl. No.: 15/148,201

(22) Filed: May 6, 2016

(65) Prior Publication Data
US 2016/0249802 A1 Sep. 1, 2016

Related U.S. Application Data

(63) Continuation of application No. PCT/JP2015/058351, filed on Mar. 19, 2015.

(30) Foreign Application Priority Data

Mar. 20, 2014 (JP) ................... 2014-059222
Mar. 9, 2015 (JP) ................... 2015-046085

(51) Int. Cl.
*A61B 3/14* (2006.01)
*A61B 3/117* (2006.01)
(Continued)

(52) U.S. Cl.
CPC ............ *A61B 3/117* (2013.01); *A61B 3/0025* (2013.01); *A61B 3/0041* (2013.01); *A61B 3/14* (2013.01);
(Continued)

(58) Field of Classification Search
CPC ........ G01N 21/21; G01N 21/23; G01N 21/39; A61B 3/10; A61B 3/14; A61B 3/117;
(Continued)

(56) References Cited

U.S. PATENT DOCUMENTS 5,209,231 A 5/1993 Cote et al.
5,243,983 A 9/1993 Tarr et al.
(Continued)

FOREIGN PATENT DOCUMENTS

CN 101160089 A 4/2008
CN 101194828 A 6/2008
(Continued)

OTHER PUBLICATIONS

May 16, 2017 Office Action issued in Chinese Patent Application No. 201580003120.X.
Jun. 2, 2015 Search Report issued in International Patent Application No. PCT/JP2015/058351.
Jun. 2, 2015 Written Opinion issued in International Patent Application No. PCT/JP2015/058351.

*Primary Examiner* — Mustak Choudhury
(74) *Attorney, Agent, or Firm* — Oliff PLC (57) ABSTRACT

An optical measuring instrument 1 is equipped with an optical system 20 to be used for measuring a characteristic of the aqueous humor in the anterior chamber 13 of an eyeball 10 of a measurement subject person and a holding unit 50 which holds the optical system 20 etc. The optical system 20 is equipped with a light emitting system 20A and a photodetecting system 20B. An optical path 28 is set so that light emitted from the light emitting system 20A passes through (traverses) the anterior chamber 13 and is detected by the photodetecting system 20B in a state that the eyeball 10 is turned outward.

5 Claims, 6 Drawing Sheets

(51) Int. Cl.
  *A61B 5/1455* (2006.01)
  *A61B 5/145* (2006.01)
  *A61B 3/00* (2006.01)
(52) U.S. Cl.
  CPC ........ *A61B 5/1455* (2013.01); *A61B 5/14532* (2013.01)
(58) Field of Classification Search
  CPC ... A61B 3/0025; A61B 3/0041; A61B 5/1455; A61B 5/14532; A61B 5/14558; A61B 5/7257; A61B 5/7207; A61B 3/102; A61B 3/112; A61B 3/113; A61B 3/165; A61B 3/0016; A61B 3/0075; A61B 3/0083; A61B 3/0091; A61B 3/0008; A61B 5/0059; A61B 5/1459; A61B 5/14507; A61B 5/14551; A61B 5/6821; A61B 5/6835; A61B 5/6843; A61B 17/0231
  USPC ..... 351/206, 219, 221, 159.73; 356/39, 301, 356/367, 368; 600/310, 318–319, 322, 600/336, 472
  See application file for complete search history.

(56) References Cited

U.S. PATENT DOCUMENTS

| | | | |
|---|---|---|---|
| 6,152,875 A | 11/2000 | Hakamata | |
| 6,246,893 B1 | 6/2001 | Gobeli | |
| 6,370,407 B1 | 4/2002 | Kroeger et al. | |
| 2003/0225321 A1* | 12/2003 | Cote | A61B 5/14558 600/318 |
| 2006/0094942 A1 | 5/2006 | Winther | |
| 2008/0218696 A1* | 9/2008 | Mir | A61B 5/14532 351/219 |

FOREIGN PATENT DOCUMENTS

| | | |
|---|---|---|
| JP | H06-503245 A | 4/1994 |
| JP | H09-138231 A | 5/1997 |
| JP | 2002-000570 A | 1/2002 |
| JP | 2003-254901 A | 9/2003 |
| JP | 3543923 B2 | 7/2004 |

* cited by examiner

EYEBALL OPTICAL MEASURING INSTRUMENT, EYEBALL OPTICAL MEASURING METHOD, AND METHOD FOR IRRADIATING AN EYEBALL AND DETECTING LIGHT COMING FROM EYEBALL

CROSS REFERENCE TO RELATED APPLICATION

This is a continuation of International Application No. PCT/JP2015/058351 filed on Mar. 19, 2015, and claims priority from Japanese Patent Application No. 2014-059222, filed on Mar. 20, 2014 and Japanese Patent Application No. 2015-046085, filed on Mar. 9, 2015.

TECHNICAL FIELD

The present invention relates to an eyeball optical measuring instrument, an eyeball optical measuring method, and a method for irradiating an eyeball and detecting light coming from the eyeball.

SUMMARY OF THE INVENTION

According to an aspect of the invention, there is provided an eyeball optical measuring instrument comprising a light emission unit that emits light toward an anterior chamber of an eyeball of a measurement subject person; a photodetection unit that detects the light that has passed through aqueous humor in the anterior chamber; and a holding unit that holds the light emission unit and the photodetection unit at such positions that the light emitted from the light emission unit passes through the anterior chamber and is detected by the photodetection unit in a state that the eyeball is turned outward.

DESCRIPTION OF SYMBOLS

1 . . . Optical measuring instrument; 10 . . . Eyeball; 11 . . . Vitreous body; 12 . . . Crystalline lens; 13 . . . Anterior chamber; 14 . . . Cornea; 15 . . . Pupil; 16 . . . Retina; 20 . . . Optical system; 20A . . . Light emitting system; 20B . . . Photodetecting system; 21 . . . Light emitting unit; 22 . . . Polarizer; 23 . . . First mirror; 24 . . . Second mirror; 25 . . . Compensator; 26 . . . Analyzer; 27 . . . Photodetecting unit; 28 . . . Optical path; 40 . . . Control unit; 50 . . . Holding unit; 51 . . . Eyepiece member; 60 . . . Calculation unit.

MODES FOR CARRYING OUT THE INVENTION

An exemplary embodiment of the present invention will be hereinafter described with reference to the accompanying drawings (optical measuring instrument 1).

Figure 1:
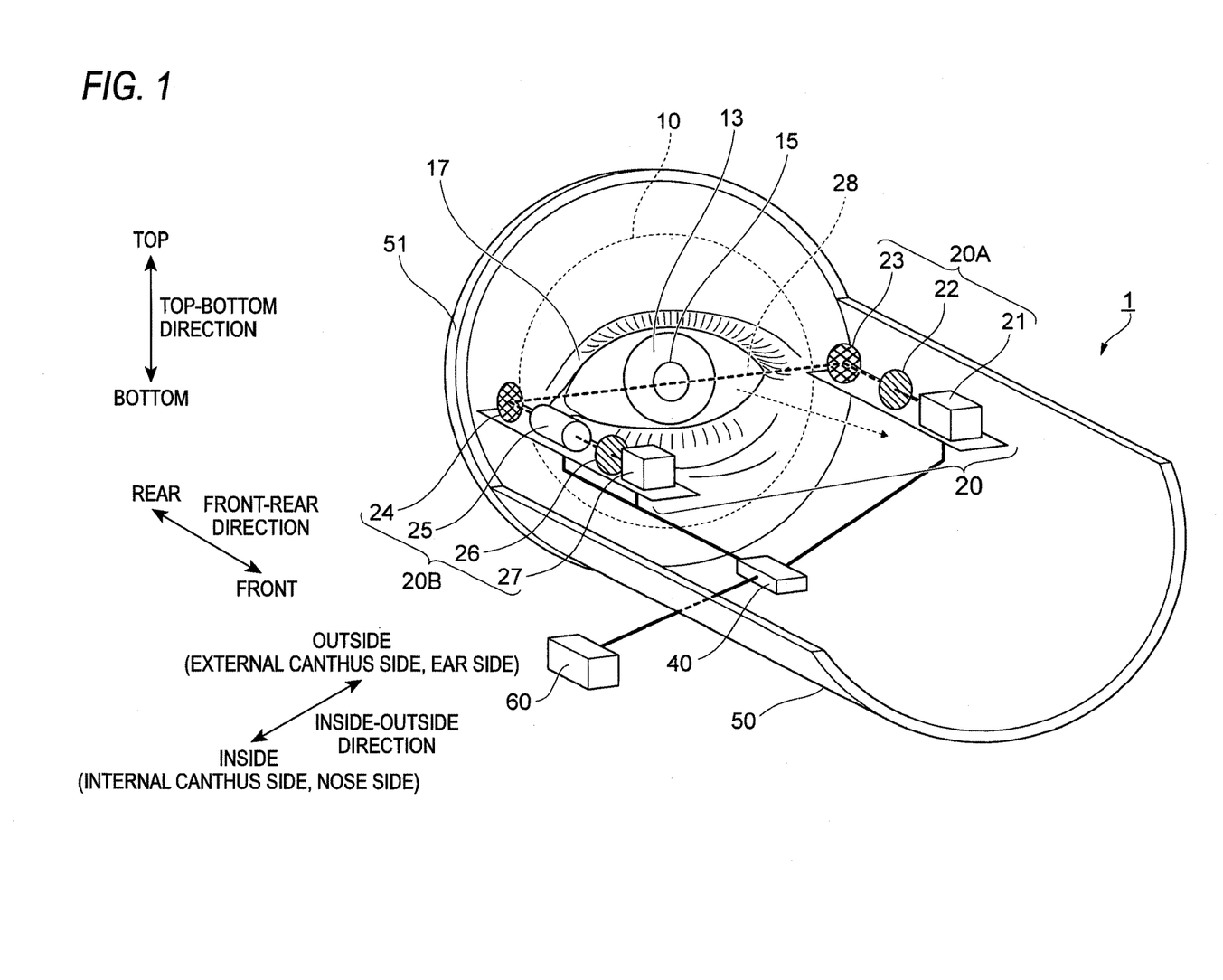
FIG. 1 shows an example configuration of an optical measuring instrument according to an exemplary embodiment.

FIG. 1 shows an example configuration of the optical measuring instrument 1 according to the exemplary embodiment.

The optical measuring instrument 1 is equipped with an optical system 20 to be used for measuring a characteristic of the aqueous humor in the anterior chamber 13 of an eyeball 10 of a measurement subject person, a control unit 40 for controlling the optical system 20, a holding unit 50 which holds the optical system 20 and the control unit 40, and a calculation unit 60 for calculating a characteristic of the aqueous humor on the basis of data measured using the optical system 20.

The eyeball 10 shown in FIG. 1 is of the left eye.

In the following description, in the optical measuring instrument 1 shown in FIG. 1, the direction connecting the top side and the bottom side of a paper surface may be referred to as the top-bottom direction. The direction connecting the front side and the rear side of the measurement subject person may be referred to as the front-rear direction. And the direction connecting the inside (internal canthus side, nose side) and the outside (external canthus side, ear side) of the measurement subject person may be referred to as the inside-outside direction.

The aqueous humor characteristic to be measured by the optical measuring instrument 1 is an angle of rotation of the polarization plane of linearly polarized light (optical rotation angle $\alpha_M$) by optically active substances contained in the aqueous humor, the degree of color absorption for circularly polarized light (circular dichroism), or the like. The term "polarization plane of linearly polarized light" means a plane in which the magnetic field of linearly polarized light oscillates.

The anterior chamber 13 of the eyeball 10 is the region between the crystalline lens 12 (see FIG. 3 (referred to later)) which serves as a lens and the cornea 14, and is filled with the aqueous humor. The anterior chamber 13 is circular when viewed from the front side. Although the eyeball 10 is approximately spherical, the anterior chamber 13 somewhat projects from the sphere surface. FIG. 1 shows a state that an eyelid 17 is open.

The optical system 20 is equipped with a light emitting unit 21, a polarizer 22, a first mirror 23, a second mirror 24, a compensator 25, an analyzer 26, and a photodetecting unit 27.

The light emitting unit 21 may be either a light source having a wide wavelength range such as a light-emitting diode (LED) or a lamp or a light source having a narrow wavelength range such as a laser. The employment of a light source having a narrow wavelength range is preferable.

The light emitting unit 21 may be one that emits light having at least two wavelengths.

The polarizer 22, which is, for example, a Nicol prism, transmits linearly polarized light having a predetermined polarization plane that is a component of incident light.

The first mirror 23 and the second mirror 24, which bend an optical path 28, are preferably such as to keep the polarization state of linearly polarized light through reflection. The use of ones that disorder the polarization state, such as ones that rotate the polarization plane or convert linearly polarized light into circularly polarized light, is not preferable. Where it is not necessary to bend the optical path 28, the first mirror 23 and/or the second mirror 24 may be omitted.

The compensator 25, which is, for example, a magneto-optical device such as a Faraday device using a garnet or the like, rotates the polarization plane of linearly polarized light using a magnetic field. The compensator 25 is not an essential part in this embodiment.

The analyzer 26, which is a member similar to the polarizer 22, transmits linearly polarized light having a predetermined polarization plane.

The photodetecting unit 27, which is a photodetecting device such as a silicon diode, outputs an output signal corresponding to light intensity.

A display unit (not shown) may be provided which displays a characteristic (e.g., a concentration of an optically active substance) of the aqueous humor calculated by the calculation unit 60.

The control unit 40 acquires measurement data relating to a characteristic of the aqueous humor by controlling the light emitting unit 21, the compensator 25, the photodetecting unit 27, etc. of the optical system 20, and sends the measurement data to the calculation unit 60.

The holding unit 50 holds the optical system 20 and the control unit 40. The holding unit 50 holds the optical system 20 so that the optical path 28 that is set in the optical system 20 goes through the aqueous humor in the anterior chamber 13 in a state that end portions of the holding unit 50 are positioned being in contact with predetermined portions near the eyeball 10. The holding unit 50 may be brought into contact with portions neighboring the eyeball 10 in such a manner that the measurement subject person or another person does so gripping the optical measuring instrument 1 with his or her own hands or a driving device moves the optical measuring instrument 1 automatically in the front-rear direction. The portions with which the holding unit 50 is to be brought into contact need not always be portions near the eyeball 10 as long as the holding unit 50 can be positioned with respect to the eyeball 10, and may be other portions of the face of the measurement subject person. The holding unit 50 need not be brought into contact with the face if it can be positioned without coming into contact with the face.

As described later, the optical path 28 (indicated by a broken line) may be set so that when the eyeball 10 is turned (outward as mentioned later), light emitted from the light emitting unit 21 passes through (traverses) the anterior chamber 13 and is detected by the photodetecting unit 27.

The sentence "light passes through (traverses) the anterior chamber 13" means that when the eyeball 10 is seen from the front side, light passes through the anterior chamber 13 in a direction that is closer to the inside-outside direction than the top-bottom direction (i.e., in a direction that forms an angle smaller than ±45° with the horizontal axis extending in the inside-outside direction); this definition includes a case that light passes through the anterior chamber 13 obliquely in the front-rear direction.

The holding unit 50 may be equipped with an eyepiece member 51 that is formed so as to fix the optical measuring instrument 1 with respect to the eyeball 10 and thereby prevent deviation of the optical path 28.

The holding unit 50 shown in FIG. 1 has a shape as obtained by cutting a cylinder by a plane that is parallel with its axial direction. However, this is to make the optical system 20 seen easily; the holding unit 50 may be cylindrical. The holding unit 50 may assume a tubular shape having an elliptical or rectangular quadrilateral cross section. Furthermore, the holding unit 50 may assume a partially cut-away cylindrical shape like the one shown in FIG. 1.

The holding unit 50 may be an eyeglass frame; that is, the optical measuring instrument 1 may be of a glasses type in which the optical system 20 and the control unit 40 are mounted on glasses.

The calculation unit 60 receives measurement data from the control unit 40 and calculates a characteristic of the aqueous humor.

In the exemplary embodiment, light that is emitted from the light emitting unit 21 goes along the optical path 28 and enters the photodetecting unit 27. More specifically, light that is emitted from the light emitting unit 21 toward the eyeball 10 side passes through the polarizer 22 and is then bent by the first mirror 23 to the direction that traverses the anterior chamber 13 (i.e., the direction parallel with the eye). Then the light passes through (traverses) the anterior chamber 13. The light is thereafter bent to such a direction as to go away from the eye. Finally, the light passes through the compensator 25 and the analyzer 26 and shines on the photodetecting unit 27.

In FIG. 1, a part including the light emitting unit 21, the polarizer 22, and the first mirror 23 is a light emitting system 20A and is an example of a light emission unit. Apart including the second mirror 24, the compensator 25, the analyzer 26, and the photodetecting unit 27 is a photodetecting system 20B which is an example of a photodetection unit.

As described later, the holding unit 50 holds the light emitting system 20A and the photodetecting system 20B in such a manner that the light emitting system 20A is deviated rearward (toward the deep side) from the photodetecting system 20B, that is, they are arranged unsymmetrically.

An arrangement may be employed that the light emitting system 20A and the photodetecting system 20B are interchanged.

Now, a description will be made of an example use of the optical measuring instrument 1 in which the aqueous humor in the anterior chamber 13 is subjected to a measurement and a glucose concentration is calculated.

In diabetics, the amount of insulin administered is controlled according to the glucose concentration in blood. Diabetics are therefore required to recognize the glucose concentration in blood all the time. The mainstream method for measuring a glucose concentration in blood is to acquire a very small amount of blood by sticking, for example, a fingertip with an injection needle. However, taking even a very small amount of blood causes suffering, that is, a pain. This is why the demand for noninvasive test methods to replace invasive test methods such as ones involving needle sticking has increased.

The aqueous humor in the anterior chamber 13 that has approximately the same components as serum contains proteins, glucose, ascorbic acid, etc. It is known that a correlation exists between the glucose concentration in blood and that in aqueous humor. Aqueous humor contains no cellular substances as found in blood and produces only small influences due to light scattering there. And proteins, glucose, ascorbic acid, etc. contained in aqueous humor are optically active substances and have optical rotatory power. As such, aqueous humor is advantageous as a part for optical measurement of a concentration of, for example, glucose utilizing optical rotatory power.

In methods for optically obtaining, for example, a concentration of an optically active substance contained in aqueous humor, the following two kinds of optical paths can be set.

One kind of optical path is an optical path for shining light on the eyeball 10 approximately perpendicularly, causing reflection of the light at the interface between the cornea 14 (see FIG. 3 (referred to later)) and the aqueous humor or the interface between the aqueous humor and the crystalline lens 12 (see FIG. 3), and receiving (detecting) the reflection light. The other kind of optical path is an optical path for shining light on the eyeball 10 at such an angle that the light goes approximately parallel with the eyeball 10 and receiving (detecting) light that has passed through the aqueous humor in the anterior chamber 13.

Figure 3:
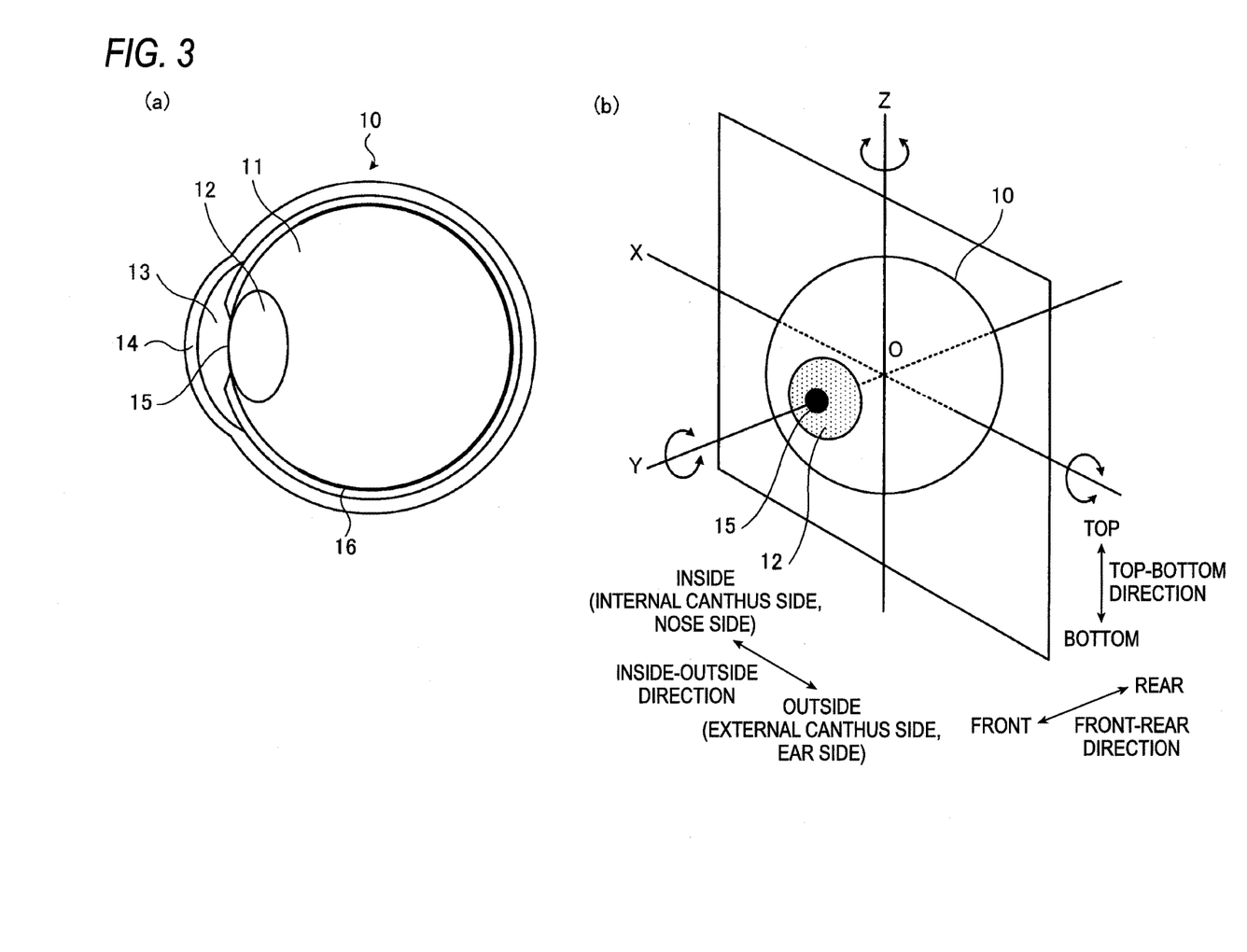

The optical path for shining light on the eyeball 10 approximately perpendicularly is associated with risk that the light reaches the retina 16 (see FIG. 3). In particular, where laser light which is high in coherence is used, light reaching the retina 16 is not preferable.

In contrast, in the case of the optical path for shining light on the eyeball 10 at such an angle that the light goes approximately parallel with the eyeball 10, light passes through the cornea 14 and then passes through (traverses) the anterior chamber 13 and resulting light that has passed through the aqueous humor is received (detected). Therefore, the probability that light reaches the retina 16 is low.

However, there are only narrow spaces where to place the light emitting unit 21, the polarizer 22, the compensator 25, the analyzer 26, the photodetecting unit 27, etc. of the optical system. 20 because the eyeball 10 has an approximately spherical outward shape and the nose (nasal bridge) exists on the light incidence side or the transmission light reception side.

In view of the above, to set the optical path 28 so that light shines on the eyeball 10 at such an angle that the light goes approximately parallel with the eyeball 10 and passes through (traverses) the anterior chamber 13, as shown in FIG. 1 the spaces are used effectively by bending the optical path 28 by disposing the first mirror 23 and the second mirror 24.

Where the optical system 20 is small, it is not necessary to bend the optical path 28.

Figure 2:
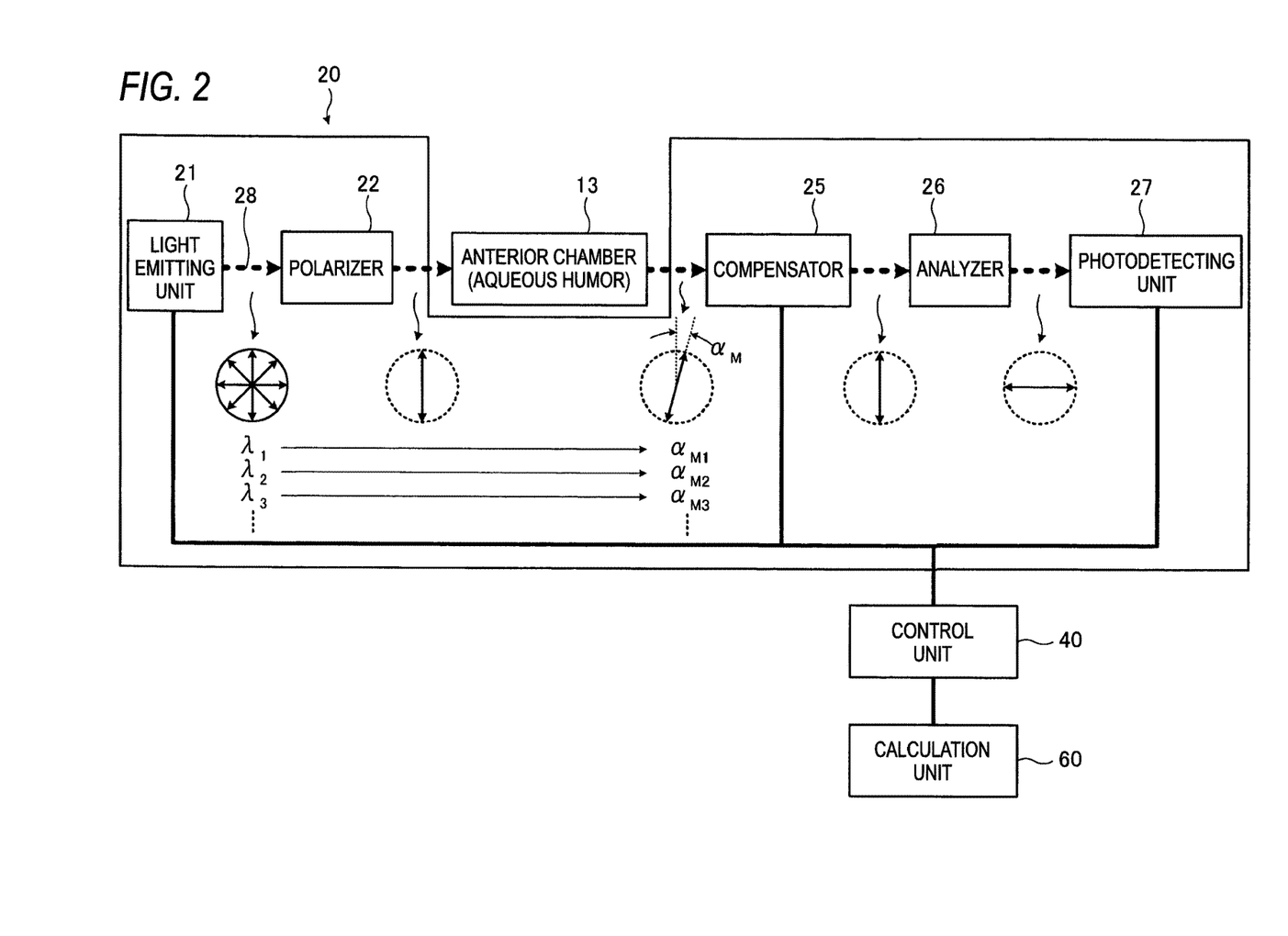
FIG. 2 illustrates a method for measuring a polarization plane rotation angle (optical rotatory power) of optically active substances contained in the aqueous humor in the anterior chamber by means of the optical measuring instrument FIG. 3 outlines an eyeball; part (a) of FIG. 3 is a vertical sectional view of the eyeball 10 and part (b) of FIG. 3 shows the coordinate system for the eyeball.

FIG. 2 illustrates a method for measuring a polarization plane rotation angle (optical rotatory power) of optically active substances contained in the aqueous humor in the anterior chamber 13 by means of the optical measuring instrument 1. In FIG. 2, to facilitate understanding, the first mirror 23 and the second mirror 24 are omitted with an assumption that the optical path 28 is not bent (i.e., it is straight).

In the optical system 20 shown in FIG. 2, polarization as viewed from the destination side of light propagation is indicated by an arrow(s) in a circle between each set of adjoining ones of the light emitting unit 21, the polarizer 22, the anterior chamber 13, the compensator 25, the analyzer 26, and the photodetecting unit 27.

It is assumed that the light emitting unit 21 emits light having random polarization planes. Receiving that light, the polarizer 22 allows passage of linearly polarized light having a predetermined polarization plane. The example of FIG. 2 is such that linearly polarized light whose polarization plane is parallel with the paper surface passes through the polarizer 22.

The linearly polarized light that has passed through the polarizer 22 is subjected to polarization plane rotation by optically active substances contained in the aqueous humor in the anterior chamber 13. In FIG. 2, it is assumed that the polarization plane is rotated by an angle $\alpha_M$ (optical rotation angle $\alpha_M$).

Then a magnetic field is applied to the compensator 25, whereby the polarization plane that has been rotated by the optically active substances contained in the aqueous humor in the anterior chamber 13 is returned to the original state.

Linearly polarized light that has passed through the analyzer 26 is received by the photodetecting unit 27 and thereby converted into an output signal corresponding to a light intensity.

An example method for measuring an optical rotation angle $\alpha_M$ using the optical system 20 will be described below.

First, the compensator 25 and the analyzer 26 are set so as to minimize the output signal of the photodetecting unit 27 in the optical system 20 including the light emitting unit 21, the polarizer 22, the compensator 25, the analyzer 26, and the photodetecting unit 27 in a state that light that is emitted from the light emitting unit 21 does not pass through the anterior chamber 13. As shown in FIG. 2, in a state that light does not pass through the anterior chamber 13, the polarization plane of linearly polarized light that has passed through the polarizer 22 is perpendicular to that of linearly polarized light that passes through the analyzer 26.

In FIG. 2, it is assumed that the polarizing plane of the polarizer 22 and the polarization plane that linearly polarized light has before passing through the analyzer 26 are both parallel with the paper surface. However, where the polarization plane is rotated by the compensator 25 in advance, the polarization plane that linearly polarized light has before passing through the analyzer 26 may be inclined from the plane that is parallel with the paper surface. That is, the compensator 25 and the analyzer 26 are set so as to minimize the output signal of the photodetecting unit 27 in a state that light that is emitted from the light emitting unit 21 does not pass through the aqueous humor in the anterior chamber 13.

Subsequently, a state that light passes through the anterior chamber 13 is established. In this state, the polarization plane is rotated by the optically active substances contained in the aqueous humor in the anterior chamber 13. As a result, the output signal of the photodetecting unit 27 deviates from the minimum value. In this state, the magnetic field that is applied to the compensator 25 is set so as to minimize the output signal of the photodetecting unit 27. That is, the polarization plane is rotated by the compensator 25 so as to become perpendicular to the polarization plane for passage through the analyzer 26.

In this state, the polarization plane rotation angle caused by the compensator 25 corresponds to an optical rotation angle $\alpha_M$ produced by the optically active substances contained in the aqueous humor. Since the relationship between the magnitude of the magnetic field applied to the compensator 25 and the polarization plane rotation angle is known in advance, an optical rotation angle $\alpha_M$ can be obtained from the magnitude of a magnetic field applied to the compensator 25.

Although in the above example an optical rotation angle $\alpha_M$ is determined using the compensator 25, an optical rotation angle $\alpha_M$ may be determined using a thing other than the compensator 25. Although the measuring method shown in FIGS. 1 and 2 show the crosses Nicols method (with the use of the compensator 25) which is the most fundamental measuring method for measuring a polarization plane rotation angle (optical rotation angle $\alpha_M$), any of other measuring methods such as the rotating analyzer method, Faraday method, and optical delay modulation method may be used.

A more specific description will be made below. Light beams having respective wavelengths $\lambda$ ($\lambda_1$, $\lambda_2$, $\lambda_3$, ...) are shone on the aqueous humor in the anterior chamber 13 from the light emitting unit 21 and optical rotation angles $\alpha_M$ ($\alpha_{M1}$, $\alpha_{M2}$, $\alpha_{M3}$, ...) are determined the respective light beams. The calculation unit 60 receives the sets of a wavelength $\lambda$ and an optical rotation angle $\alpha_M$ and calculates a concentration of a target optical active substance.

As mentioned above, the aqueous humor contains plural optically active substances. Therefore, each measured optical rotation angle $\alpha_M$ is the sum of optical rotation angles $\alpha$ of the plural respective optically active substances. It is therefore necessary to calculate a concentration of the target optical active substance from the measured optical rotation angles $\alpha_M$.

A concentration of the target optical active substance may be calculated by a known method as disclosed in, for example, JP-A-09-138231 (above-mentioned Patent document 2), and hence a description therefor is omitted here.

FIG. 3 outlines the eyeball 10. Part (a) of FIG. 3 is a vertical sectional view of the eyeball 10 and part (b) of FIG. 3 shows the coordinate system for the eyeball 10.

As shown in part (a) of FIG. 3, the eyeball 10 has an approximately spherical outward shape and has the vitreous body 11 at the center. The crystalline lens 12 which serves as a lens is buried in the vitreous body 11. The anterior chamber 13 is located outside the crystalline lens 12 and the cornea 14 is located outside the anterior chamber 13. The crystalline lens 12 is surrounded by the iris, and a central portion of crystalline lens 12 is the pupil 15. The vitreous body 11 is covered with the retina 16 except a portion that is in contact with the crystalline lens 12.

That is, the anterior chamber 13 is the portion that is surrounded by the cornea 14 and the crystalline lens 12, and projects from the sphere of the eyeball 10 so as to assume a convex shape. The anterior chamber 13 is filled with the aqueous humor.

It is assumed that the eyeball 10 shown in part (b) of FIG. 3 is of the left eye and is directed to the front side. That is, the left side and the right side as viewed from the viewer's side are the internal canthus side (nose side) is the external canthus side (ear side), respectively. The X axis is defined as the axis that goes right to left (when viewed from the viewer's side) passing through the center O (rotation center) of a turn of the eyeball 10, the Y axis is defined as the axis that goes from the deep side to the viewer's side, and the Z axis is defined as the axis that goes from the bottom side to the top side.

A turn of the eyeball 10 about the Z axis toward the internal canthus side (nose side) will be referred as an "inward turn," and a turn of the eyeball 10 about the Z axis toward the external canthus side (ear side) will be referred as an "outward turn." The directions of the inward turn and the outward turn of the right eye are opposite to those of the left eye.

Incidentally, an upward turn of the eyeball 10 about the X axis is called an "upward turn," and a downward turn of the eyeball 10 about the X axis is called a "downward turn." And a rotation of the eyeball 10 about the Y axis is called a "rotation."

The term "outward turn" includes not only a turn toward the external canthus side (ear side) from a state that the eyeball 10 (pupil 15) is directed to the front side but also a turn toward the external canthus side (ear side) in a state that the eyeball 10 (pupil 15) is turned upward (e.g., by +45° or less toward the Z axis) or downward (e.g., by −45° or less toward the Z axis).

Similar things apply to the term "internal turn."

Figure 4:
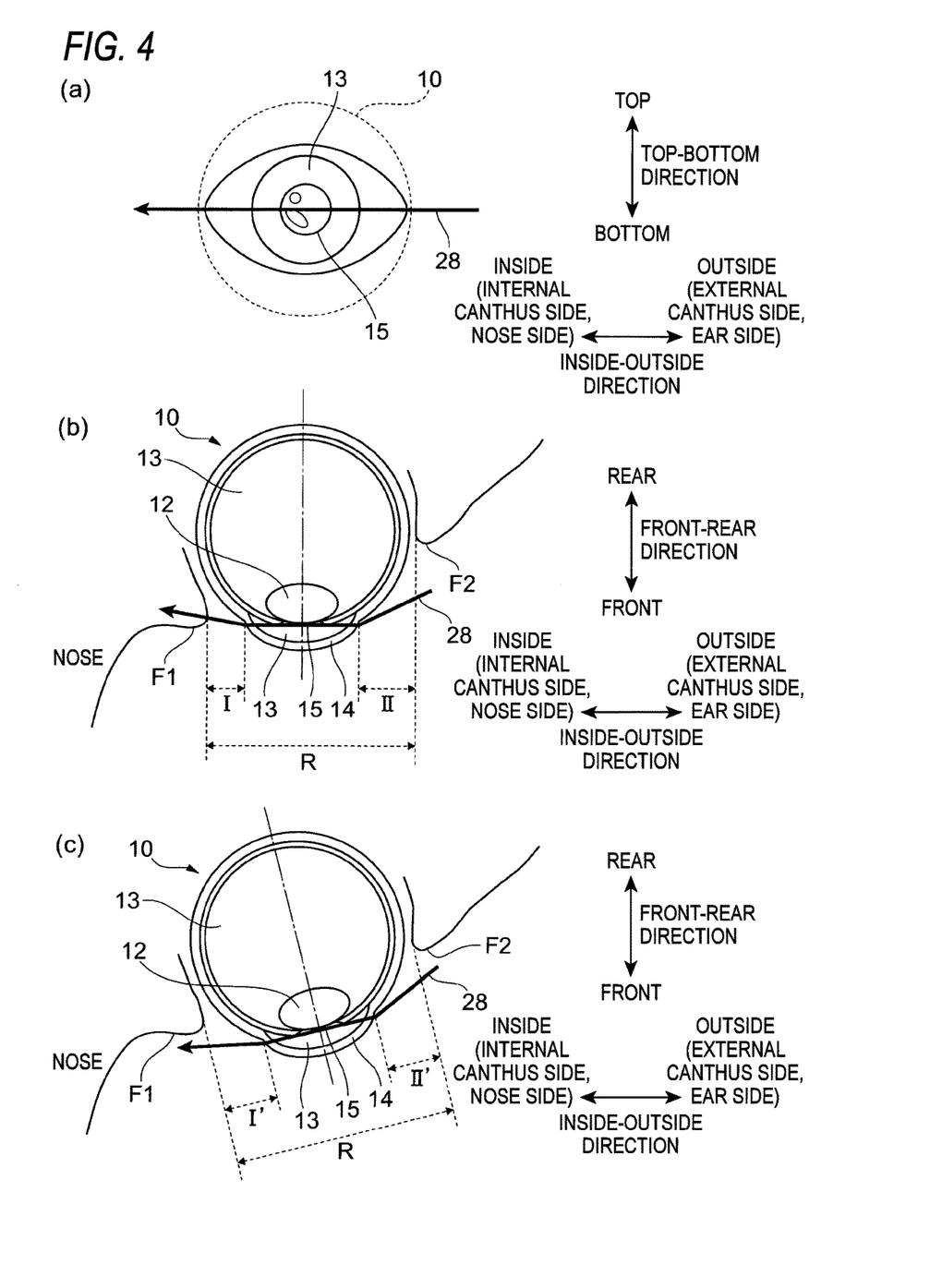
FIG. 4 illustrates relationships between the eyeball and optical paths; part (a) of FIG. 4 is a front view of the eyeball, part (b) of FIG. 4 shows an optical path that occurs in a state that the eyeball is directed to the front side, and part (c) of FIG. 4 shows an optical path that occurs in a state that the eyeball is turned outward.

FIG. 4 illustrates relationships between the eyeball 10 and the optical paths 28. Part (a) of FIG. 4 is a front view of the eyeball 10, part (b) of FIG. 4 shows an optical path 28 that occurs in a state that the eyeball 10 is directed to the front side, and part (c) of FIG. 4 shows an optical path 28 that occurs in a state that the eyeball 10 is turned outward. Parts (b) and (c) of FIG. 4 show states that the person is viewed from the top (i.e., from above). These figures were drawn by simulations using a face model.

As shown in part (a) of FIG. 4, the optical path 28 is set so that light goes from the external canthus side (ear side) to the internal canthus side (nose side), to facilitate the description. The optical path 28 may be set so that light goes from the internal canthus side (nose side) to the external canthus side (ear side).

As shown in part (b) of FIG. 4, when the eyeball 10 is directed to the front side, light that is emitted from the light emitting system 20A (see FIG. 1) passes through the cornea 14 and shines on the anterior chamber 13. Since the refractive indices of the cornea 14 and the aqueous humor in the anterior chamber 13 are larger than the refractive index of air and the anterior chamber 13 and the cornea 14 are convex, the light (optical path 28) is bent toward the eyeball 10 side. In leaving the anterior chamber 13, the light is also bent toward the eyeball 10 side. Thus, after passing through the anterior chamber 13, the light takes a locus that is closer to the face surface.

In ordinary persons, an internal-canthus-side skin portion F1 is closer to the front side than an external-canthus-side skin portion F2. Furthermore, the nose exists on the internal canthus side. When the eyeball 10 is directed to the front side, there may occur a situation that it is difficult to secure, on the internal canthus side, a space where to place the photodetecting system 20B (see FIG. 1).

If the photodetecting system 20B can be placed at a position that is very close to the eyeball 10 (e.g., a position that is very close to a white portion I of the eye in a region R where the eyeball 10 is exposed from the skin portions F1 and F2), the presence of the internal-canthus-side skin portion F1 and the nose can be disregarded. However, in this case, a member of the photodetecting system 20B is prone to touch the eyeball 10.

On the other hand, as shown in part (c) of FIG. 4, when the eyeball 10 is turned outward, that is, when the line of sight is directed to the external canthus side (ear side), light that is emitted from the light emitting system 20A passes through the cornea 14 and shines on the anterior chamber 13. In this case, since the eyeball 10 is turned outward, after passing through the anterior chamber 13, the light takes a locus that is more distant from the face surface than in the case of part (b) of FIG. 4.

Turning the eyeball 10 outward increases the internal-canthus-side space and thereby makes it easier to place the photodetecting system 20B on the internal canthus side than in the case shown in part (b) of FIG. 4 where the eyeball 10 is directed to the front side. That is, utilizing the increased space on the internal canthus side, the photodetecting system 20B can be placed on the internal-canthus-side skin portion F1 between the nose and the region R where the eyeball 10 is exposed. In this case, since the members constituting the photodetecting system 20B are set distant from the eyeball 10, the probability that a member of the photodetecting system 20B touches the eyeball 10 is lowered.

Even where the photodetecting system 20B is placed close to an exposed white portion I' of the eyeball 10, the white portion I' is wider and is more distant from the optical path 28 than the white portion I of the case shown in part (b) of FIG. 4 that the eyeball 10 is directed to the front side. Therefore, by placing the photodetecting system 20B at a position that is more distant from the eyeball 10, the probability that a member of the photodetecting system 20B touches the eyeball 10 is lowered.

On the other hand, on the external canthus side, when the eyeball 10 is turned outward, the space is made narrower than in the case shown in part (b) of FIG. 4 that the eyeball 10 is directed to the front side. However, since originally a wide space can be secured more easily on the external canthus side than on the internal canthus side, the light emitting system 20A can be placed close to an exposed white portion II', on the external-canthus-side skin portion F2, or outside it.

The probability that a member of the light emitting system 20A or the photodetecting system 20B touches the eyeball 10 can be lowered by placing the light emitting system 20A and the photodetecting system 20B outside the region R where the eyeball 10 is exposed on both of the internal canthus side and the external canthus side (e.g., on the skin portions F1 and F2) rather than inside the region R. With this measure, the probability that a member touches the eyeball 10 is lower even if the light emitting system 20A or the photodetecting system 20B is deviated in the front-rear direction. It suffices that the light emitting system 20A or the photodetecting system 20B be placed outside the region R where the eyeball 10 is exposed on at least the internal canthus side and the external canthus side.

The above description is directed to the case that the optical path 28 is set so that light goes from the external canthus side (ear side) to the internal canthus side (nose side). The same concept applies to the case that the optical path 28 is set so that light goes from the internal canthus side (nose side) to the external canthus side (ear side). That is, read "light emitting system 20A" in the above description as "photodetecting system 20B" and vice versa.

In the exemplary embodiment, the phrases "on the skin portion F1" and "on the skin portion F2" each include both of a state that contact is made to the skin and a state that contact is not made to the skin, that is, mean a state that the system concerned coexists with the skin portion when the eyeball 10 is viewed from the front side.

Deviation of the optical path 28 from the anterior chamber 13 may disable a correct measurement. That is, a more correct measurement is enabled by setting the optical path 28 so that light traverses the anterior chamber 13 without deviating from it. The optical rotation angle $\alpha_M$ is affected by the optical path length which is the length over which light passes through the aqueous humor in the anterior chamber 13. Therefore, if the portion concerned of the optical path 28 is short, a relative variation between the optical path length over which light actually travels and the optical path length for calculation of an optical rotation angle $\alpha_M$ tends to be large and hence the measurement accuracy tends to be lower than in a case that the portion concerned of the optical path 28 is long.

In the exemplary embodiment, since the optical path is set so as to traverses the anterior chamber 13, the optical path length can be set longer than in the above-described case that light shines on the eyeball 10 approximately perpendicularly. This makes it easier to increase the measurement accuracy than in the case that light is incident approximately perpendicularly.

Figure 5:
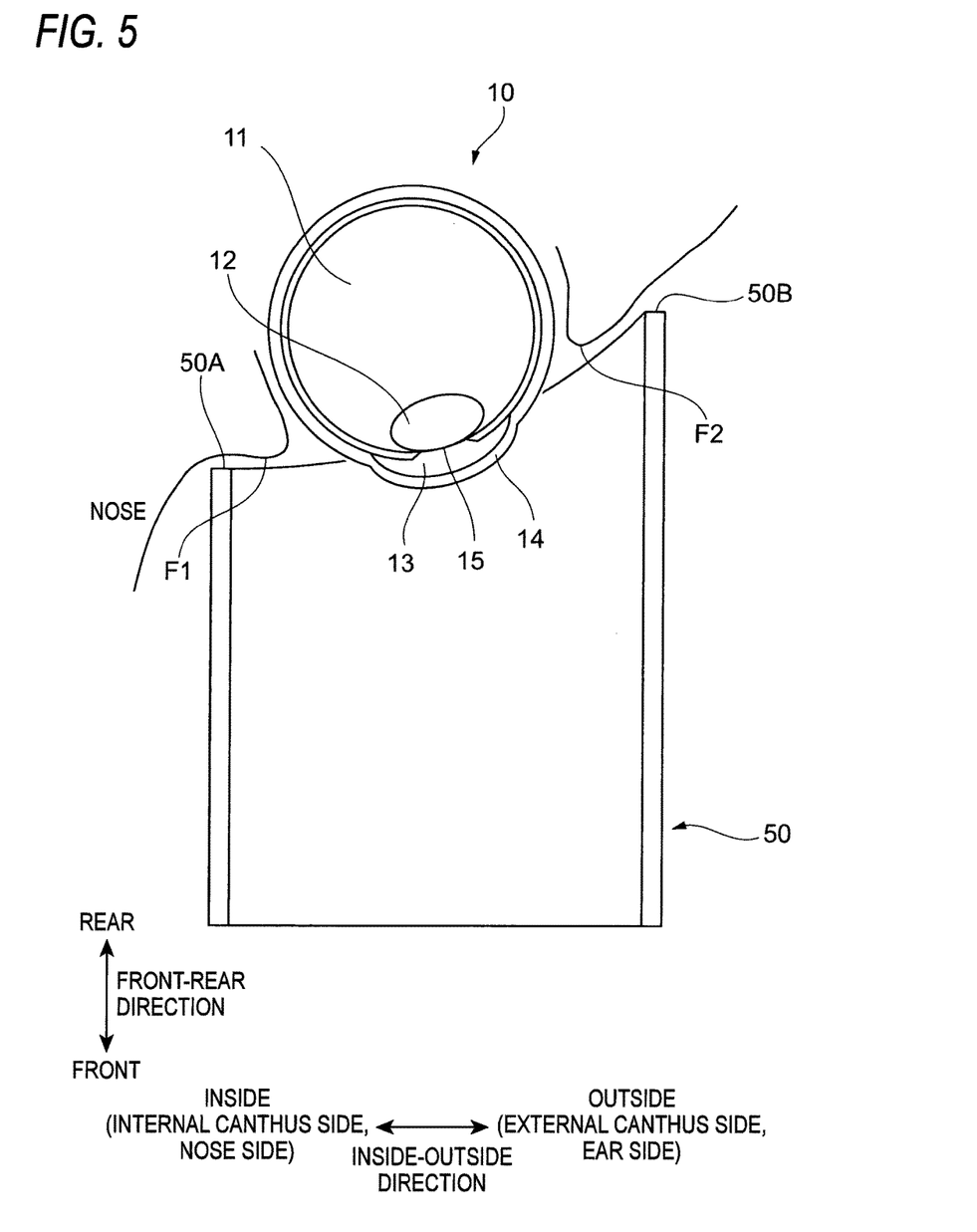
FIG. 5 illustrates an example method for placing a holding unit with respect to a face.

FIG. 5 illustrates an example method for placing the holding unit 50 with respect to a face.

As described above with reference to FIG. 4, in ordinary persons, the internal-canthus-side skin portion F1 is closer to the front side than the external-canthus-side skin portion F2. In view of this, the holding unit 50 is formed so as to conform to the shapes (undulation) of the internal-canthus-side skin portion F1 and the external-canthus-side skin portion F2 of the face. More specifically, an external-canthus-side end portion 50B to come into contact with the external-canthus-side skin portion F2 deviates rearward (toward the deep side) from an end portion 50A to come into contact with the internal-canthus-side skin portion F1. In other words, the holding unit 50 is formed in such a manner that its internal-canthus-side portion and external-canthus-side portion are asymmetrical with each other. Likewise, the light emitting system 20A and the photodetecting system 20B which are held by the holding unit 50 deviate from each other so that the one placed on the internal canthus side is located on the front side, in the front-rear direction respective to the eyeball 10, of the one placed on the external canthus side.

(Optical Measuring Method and Method for Irradiating an Eyeball and Detecting Light Coming from the Eyeball)

Figure 6:
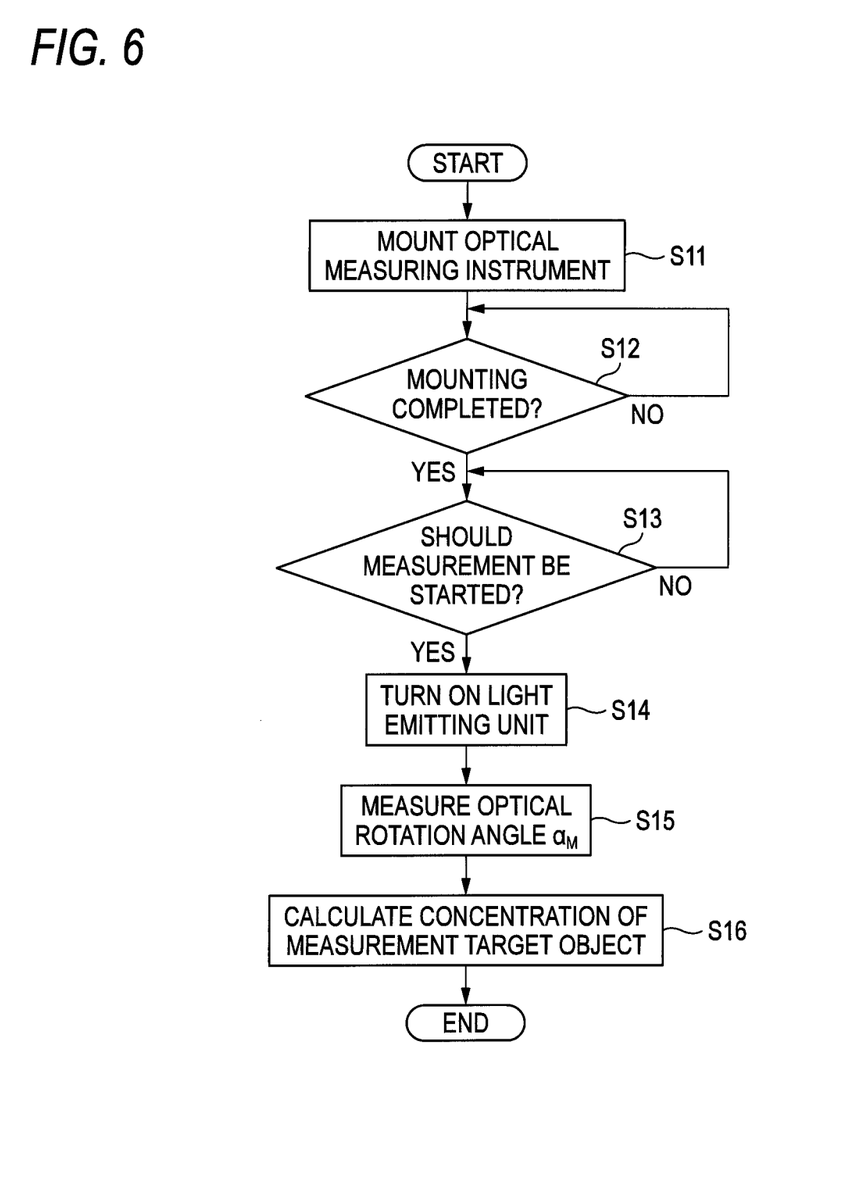
FIG. 6 is a flowchart for description of an optical measuring method for measuring a concentration of an optically active substance contained in the aqueous humor in the anterior chamber and a method for irradiating the eyeball and detecting light coming from the eyeball.

FIG. 6 is a flowchart for description of an optical measuring method for measuring a concentration of an optically active substance contained in the aqueous humor in the anterior chamber 13 and a method for irradiating the eyeball 10 and detecting light coming from the eyeball.

First, a measurement subject person powers on the optical measuring instrument 1 and has it attached to himself or herself (step 11; denoted by S11 in FIG. 6 (this kind of notation applies to the other steps)). Upon being powered on, the optical measuring instrument 1, the optical system 20, the control unit 40, and the calculation unit 60 are rendered operational.

Then the control unit 40 judges whether or not the measurement subject person has completed mounting of the optical measuring instrument 1 (step 12). For example, the optical measuring instrument 1 is equipped with a button for notification of mounting completion and the measurement subject person pushes it upon completion of mounting of the optical measuring instrument 1. And the control unit 40 judges whether or not the measurement subject person has completed mounting of the optical measuring instrument 1 according to whether the button for notification of mounting completion has been pushed or not.

If a negative judgment ("no") is made at step 12, that is, if mounting has not completed yet, the process returns to step 12 to wait for completion of mounting.

On the other hand, if an affirmative judgment ("yes") is made, then the control unit 40 judges whether to start a measurement (step 13). For example, the optical measuring instrument 1 is equipped with a button for commanding a measurement start and the measurement subject person pushes it upon completion of mounting of the optical measuring instrument 1. And the control unit 40 judges whether to start a measurement according to whether the button for commanding a measurement start has been pushed or not.

If a negative judgment ("no") is made at step 13, that is, if a measurement should not be started, the process returns to step 13 to wait for a time to start a measurement.

On the other hand, if an affirmative judgment ("yes") is made, that is, if a measurement start has been commanded, the control unit 40 causes the light emitting unit 21 of the light emitting system 20A to emit light (step 14) and causes a measurement of an optical rotation angle $\alpha_M$ of light that has passed through the aqueous humor in the anterior chamber 13 (step 15). Then the control unit 40 sends measurement data such as the measured optical rotation angle $\alpha_M$ to the calculation unit 60.

In response, the calculation unit 60 calculates a concentration of a target optical active substance (measurement target object) contained in the aqueous humor in the anterior chamber 13 (step 16).

Although the method for calculating a concentration of a target optical active substance contained in the aqueous humor has been described as an example with reference to the flowchart of FIG. 6, a configuration is possible that measures another characteristic of aqueous humor.

The configuration described in the exemplary embodiment may be applied to determination of a characteristic relating to, for example, the cornea 14 existing on the optical path 28 instead of a characteristic of the aqueous humor. More specifically, the configuration described in the exemplary embodiment can be applied to any of other cases in which a characteristic relating to the eyeball 10 is determined by shining light on the eyeball 10 from outside and causing the light to pass through the cornea 14 and the aqueous humor in the anterior chamber 13.

Although the exemplary embodiment has been described using the left eye, the invention can be applied to a measurement on the right eye. The direction of the outward turn of the eyeball 10 is such a direction that the pupil 15 goes away from the nose, and the optical path 28 may be set so that light that is emitted from the light emitting system 20A passes through (traverses) the anterior chamber 13 and is detected by the photodetecting system 20B.

Although the mode that the holding unit 50 holds the light emitting system 20A and the photodetecting system 203 in such a manner that the former deviates from the latter rearward (toward the deep side), that is, they are asymmetrical with each other, is disclosed in the exemplary embodiment, the invention is not necessarily limited to that mode. A mode (configuration) is possible that the light emitting system 20A and the photodetecting system 20B are held symmetrically with each other as long as light can be shone and detected so as to traverse the anterior chamber 13 of the eyeball 10 with the eyeball 10 turned outward. Asymmetrical configurations other than the one disclosed in the exemplary embodiment may also be employed.

Furthermore, the control unit 40 and the calculation unit 60 may be integrated with each other. Data exchange between the control unit 40 and the calculation unit 60 may be performed either by wire or wirelessly.

The optical measuring instrument etc. according to the invention are useful for acquisition of a characteristic of the aqueous humor of an eyeball.

Although the invention has been described in detail by referring to the particular exemplary embodiment, it is apparent to those skilled in the art that various changes and modifications are possible without departing from the spirit and scope of the invention.

The present application is based on Japanese Patent Application No. 2014-059222 filed on Mar. 20, 2014 and No. 2015-046085 filed on Mar. 9, 2015, the disclosures of which are incorporated herein by reference.

The invention claimed is:

1. An eyeball optical measuring instrument comprising:
   a light source that emits light toward an anterior chamber of an eyeball of a measurement subject person;
   a photodetecting device that detects the light that has passed through aqueous humor in the anterior chamber; and
   a holding device that has (a) an external canthus side end portion that comes into contact with the measurement subject person on an external canthus side of the eyeball and (b) an internal canthus side end portion that comes into contact with the measurement subject person on an internal canthus side of the eyeball, the external canthus side end portion deviating rearward from the internal canthus side end portion, the holding device holding the light source and the photodetecting device at such positions that the light emitted from the light source passes through so as to traverse the anterior chamber and is detected by the photodetecting device in a state where a line of sight of the eyeball is directed to the external canthus side of the eyeball,
   wherein the holding device holds the light source and the photodetecting device so that one of the light source and the photodetecting device placed on the internal canthus side of the eyeball is located on a front side, in a front-rear direction respective to the eyeball, of an other of the light source and the photodetecting device placed on the external canthus side of the eyeball.

2. The eyeball optical measuring instrument according to claim 1, wherein the holding device holds the light source and the photodetecting device in such a manner that at least one of them is placed outside a region where the eyeball is exposed.

3. The eyeball optical measuring instrument according to claim 1, wherein the holding device holds the light source and the photodetecting device in such a manner that both of them are placed outside a region where the eyeball is exposed.

4. An eyeball optical measuring method comprising:
   causing light to pass through an anterior chamber of an eyeball of a measurement subject person in such a manner as to traverse the anterior chamber in a state where a line of sight of the eyeball is directed to an external canthus side of the eyeball;
   holding, using a holding device, a light source that emits light toward an anterior chamber of an eyeball of a measurement subject person and a photodetecting device that detects the light that has passed through aqueous humor in the anterior chamber so that one of the light source and the photodetecting device placed on an internal canthus side of the eyeball is located on a front side, in a front-rear direction respective to the eyeball, of an other of the light source and the photodetecting device placed on the external canthus side of the eyeball, the holding device having (a) an external canthus side end portion that comes into contact with the measurement subject person on the external canthus side of the eyeball and (b) an internal canthus side end portion that comes into contact with the measurement subject person on the internal canthus side of the eyeball, the external canthus side end portion deviating rearward from the internal canthus side end portion; and
   detecting the light that has passed through the aqueous humor in the anterior chamber.

5. A method for irradiating an eyeball and detecting light coming from the eyeball, comprising:

shining light on an anterior chamber of an eyeball in a state where a line of sight of the eyeball is directed to an external canthus side of the eyeball;

holding, using a holding device, a light source that emits light toward an anterior chamber of an eyeball of a measurement subject person and a photodetecting device that detects the light that has passed through aqueous humor in the anterior chamber so as to traverse the anterior chamber, so that one of the light source and the photodetecting device placed on an internal canthus side of the eyeball is located on a front side, in a front-rear direction respective to the eyeball, of an other of the light source and the photodetecting device placed on the external canthus side of the eyeball, the holding device having (a) an external canthus side end portion that comes into contact with the measurement subject person on the external canthus side of the eyeball and (b) an internal canthus side end portion that comes into contact with the measurement subject person on the internal canthus side of the eyeball, the external canthus side end portion deviating rearward from the internal canthus side end portion; and     detecting the light that exits the eyeball after traversing the anterior chamber.

\* \* \* \* \*